United States Patent [19]

Hirel et al.

[11] 4,324,663
[45] Apr. 13, 1982

[54] METHOD AND APPARATUS FOR REGULATING HAEMODIALYSIS CONDITIONS

[75] Inventors: Jean C. Hirel, Villebon-sur-Yvette; François M. Goupy, Paris; Pierre G. Bloch, Sceaux; Patrice E. Dégoulet, Paris, all of France

[73] Assignee: Institut National de la Santé et de la Recherche Médicale, Paris, France

[21] Appl. No.: 820,642

[22] Filed: Aug. 1, 1977

[30] Foreign Application Priority Data

Jul. 30, 1976 [FR] France .............................. 76 23423

[51] Int. Cl.³ ............................................. B01D 13/00
[52] U.S. Cl. .................................. 210/646; 210/321.2
[58] Field of Search ...................... 210/22, 23, 85, 87, 210/90, 96, 97, 103, 138, 188, 321, 416, 433

[56] References Cited

U.S. PATENT DOCUMENTS 3,946,731  3/1976  Lichtenstein ........................ 210/22
3,990,973  11/1976  Boag et al. .................. 210/321 B X Primary Examiner—S. Leon Bashore
Assistant Examiner—Ferris H. Lander
Attorney, Agent, or Firm—A. W. Breiner

[57] ABSTRACT

This invention relates to the regulation of the conditions of haemodialysis by ultrafiltration of the blood wherein ultrafiltration conditions are regulated automatically as a function of the difference between the actual weight of the patient and a predetermined area of acceptable weights at any stage during the course of haemodialysis, which area will generally include an ideal curve which the patient's weight will be constrained to follow during the course of haemodialysis. This invention is applicable to the treatment of invalids having chronic renal disease.

12 Claims, 6 Drawing Figures

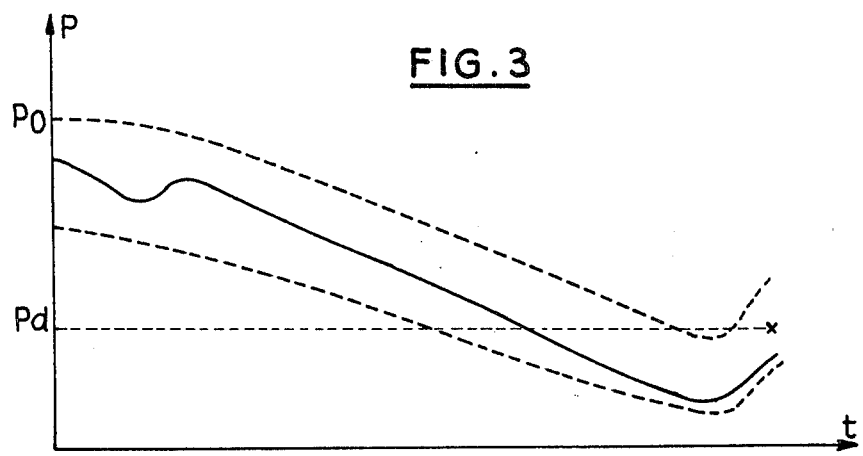
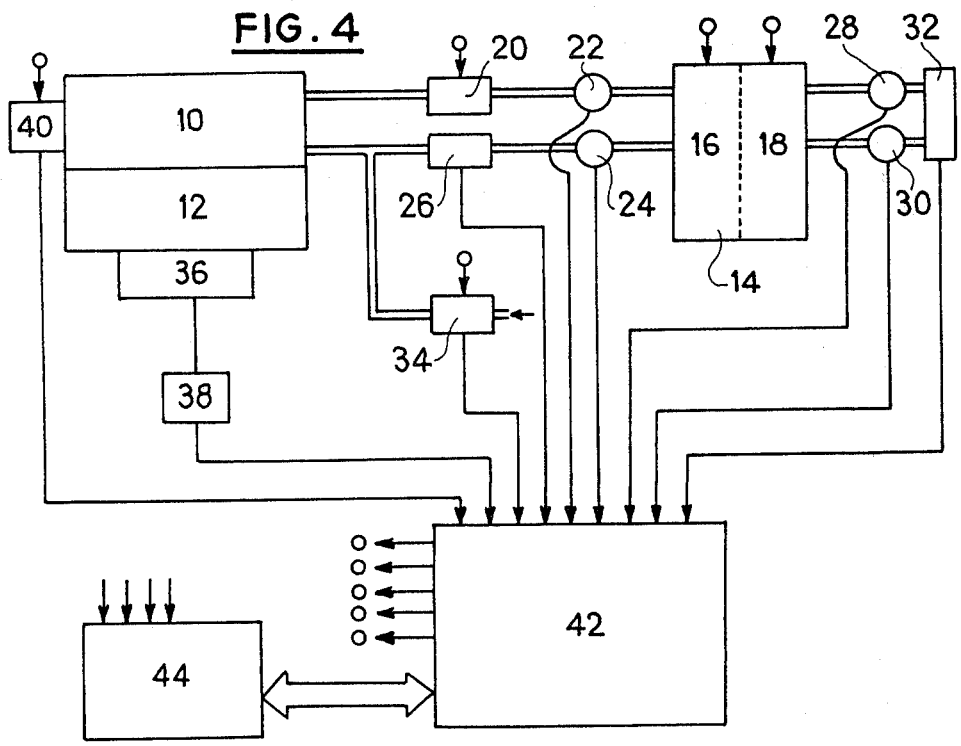

METHOD AND APPARATUS FOR REGULATING HAEMODIALYSIS CONDITIONS

This invention relates to a method and apparatus for purification of blood by extra-corporeal haemodialysis. More specifically, this invention is concerned with regulating haemodialysis conditions in effecting purification of blood extra-renally so that the dangers of accidents are reduced.

To overcome chronic renal insufficiency, use is made of artificial kidneys or haemodialysers. Apparatus of this type achieves purification of blood by circulation of the blood of the patient and of a solution, separated by a diaphragm, circulation preferably being in counter-current. The purification which occurs utilises the phenomena of diffusion, osmosis and usually ultrafiltration.

Three types of dialyser have found common use, these dialysers differing basically in respect of the arrangement of the blood compartment and solution compartment and being termed: coil dialysers, plate dialysers and capillary dialysers. Reference is here made to an article by A. Baglin and J. P. Fendler "L'hemodialyse periodique", Revue de Medicine, No. 4, Jan. 28, 1974, pages 107 to 111, which describes in detail the principles of haemodialysis and artificial kidneys which are used therein.

During a haemodialysis session, which may, for example, last for 6 to 8 hours, patients often exhibit hypotension. This phenomenon can quickly lead to serious consequences for the patient and, for this reason, must be remedied as soon as it is noticed. Various procedures have been proposed for noting the fluid loss responsible for blood pressure drop and remedying it. For example, U.S. Pat. No. 3,228,397 describes an arrangement for controlling flow of liquid circulating in a patient, particularly at the time of a perfusion or during haemodialysis. This arrangement comprises a beam balance, a displacement of which as a patient undergoes excessive fluid loss controls a parameter which causes variation in the flow of fluid to and from the patient, so that the body weight of the patient remains practically constant.

U.S. Pat. No. 3,441,136 describes a blood dialysis apparatus constructed so as to allow control of certain parameters of the dialysis fluid and blood, and especially the arterial pressure. A logic unit assures the programming of the functioning the total system which comprises a computer, a display console and a warning arrangement. This system serves to control the nature of the fluid used during the dialysis, but does not provide any check or automatic control of the haemodialysis itself.

French Pat. No. 2,242,998 and the published Federal German Patent Application No. 1,566,661 describe the measurement of arterial pressure by a method not involving passage of blood through test apparatus. French Pat. Nos. 2,209,929 and 2,078,225 describe apparatus for weighing a patient to determine whether fluid loss is occurring.

Of particular interest in this connection is an article entitled "Automatic Fluid Replacement and Blood Pressure Control During Dialysis", Vol. XVI, Trans. Amer. Soc. Artif. Int. Organs, 1970, J. A. Miller, E. Prescott and C. Carpenter which describe the automatic adjustment of haemodialysis conditions with the object of raising blood pressure when hypotension occurs, by comparison of the weight of a patient with a theoretical weight which he should have so that a perfusion or intravenous drip is actuated to replenish body fluid lost when the actual weight is lower than the normal body weight of the patient thereby causing the hypotension. This perfusion is stopped when the weight has re-assumed the desired value. The automatic adjustment of haemodialysis conditions also includes the modification of the transmembrane pressure gradient so that the speed of ultrafiltration increases when the body weight becomes too high and the further adjustment of this pressure gradient when the desired weight has been reached, comparison of the blood pressure of the patient with a predetermined alarm point, reduction of the transmembrane pressure gradient to a minimum value when the blood pressure falls below the alarm point and immediate initiation of a perfusion, triggering of an alarm circuit indicating to the staff that the blood pressure has fallen and stopping of perfusion and returning to its previous value the transmembrane pressure gradient when the blood pressure has returned to above the alarm point.

In this article by Miller et al, it is proposed that the arterial pressure be measured by a sensor placed on the arterial channel of the haemodialyser. In the event of a fall in arterial pressure, the apparatus operates to reduce the transmembrane pressure to a minimum value and immediately starts a perfusion. It simultaneously triggers an external alarm. When the pressure rises again to above the alarm point, the apparatus terminates the perfusion and increases the transmembrane pressure.

It has now been discovered that an automatic haemodialysis apparatus should satisfy a condition which is not fulfilled by apparatus described in the aforesaid article by Miller et al. This is a condition whereby the patient can be allowed to undergo weight change during haemodialysis, provided that this weight change is in accordance with a weight/time curve which can be calculated and which is based upon certain initial values of dialysis parameters and the desired final body weight and which lies within predetermined acceptable limits. More particularly it has been found that the hypotension phenomenon which is particularly dangerous is not the cause of the established incidents but is a simple result thereof. In this connection, it is the variation in weight loss over a period of time which is the main parameter to take into consideration and this has to be controlled very precisely during haemodialysis.

This invention provides a haemodyalsis apparatus for effecting dialysis of the blood by ultrafiltration, comprising: a haemodialyser having membrane means separaing a blood compartment from a dialysis solution compartment, means for causing the circulation of the blood of a patient and a haemodialysis solution on either side of said membrane, a perfusion arrangement for a patient whose blood is to undergo haemodialysis, and a plurality of sensors, comprising: at least one sensor of a parameter related to the weight of a patient for providing a signal representing variations in the weight of the patient, at least one sensor of arterial pressure adapted to provide a signal indicating the magnitude of arterial pressure, and at least one sensor of a parameter determining the course of ultrafiltration, this sensor being adapted to provide at least one ultrafiltration signal, the sensors being associated with means for comparing the signal of variations in weight with an area of weight values defined by plotting maximum and minimum acceptable weights of the patient against time within a haemodialysis period during which the haemodialyser is to be employed, to give a deficiency signal when the signal of weight variation is not within said area.

This invention is also concerned with an arrangement designed to cause variation in the limits of the weight value area as a function of time during the haemodialysis. Preferably, this area is modified so that it always incorporates an ideal curve of which the variations as a function of time are predetermined. This modification of the predetermined variation in a reference value can be effected during the course of a haemodialysis.

According to a preferred embodiment, the apparatus comprises additional means for comparing at least one signal defining the course of ultrafiltration with a second area of values. Any deviation from this second area will give rise to a second deficiency signal. When a deficiency is registered, whatever the parameter concerned, it is preferable that an alarm indicating arrangement be associated with the respective comparing means in order that the existence of a deficiency signal should be indicated by the alarm indicating arrangement.

The apparatus also preferably comprises a control means intended for modifying the value of one of the parameters defining the course of ultrafiltration when a deficiency signal is being produced. This parameter is preferably the speed of perfusion or drip. The parameter which defines the course of ultrafiltration which is monitored is generally selected from the weight of the liquid withdrawn by ultrafiltration, the blood pressure at the inlet to the haemodialyser, the blood pressure at the outlet from the haemodialyser, the pressure of the haemodialyser solution at the inlet to the haemodialyser, the pressure of the haemodialysis solution at the outlet from the haemodialyser, the rate of flow of blood in the haemodialyser and the rate of perfusion during the haemodialysis.

The apparatus also preferably comprises a display console adapted to receive signals representing the variations in weight of the patient and signals representing the area as aforesaid of the weight/time curve and adapted to display curves which represent the limits of said area of weight values and variations in the weight of the patient during the haemodialysis.

The measurement of arterial pressure is preferably by means of a bloodless procedure and is advantageously carried out by detection of the Korotkoff sounds or by Doppler effect.

This invention is also concerned with a method of regulating haemodialysis conditions while simultaneously subjecting a patient to ultrafiltration of the blood, which method comprises: circulating the blood of the patient to and from one side of a membrane of a haemodialyser, circulating a haemodialysis solution to and from the other side of the said membrane of the haemodialyser, supplying physiologically acceptable fluid to the patient by perfusion, controlling variations in the weight of the patient due to the haemodialysis, controlling the arterial pressure of the patient, and controlling at least one parameter determining the course of ultrafiltration, determining a validity zone defined by two weight/time curves defining at any given moment an area of weight values and comparing variations in weight with said area at any one moment, and utilising the comparisons in the maintenace of said control.

Preferably, the method of the invention comprises the modification of one parameter of the ultrafiltration and there is an indication of the deviation from a prescribed value area. The value area with which is compared the variation parameter of the weight of the patient, is defined at any moment by a range which is determined by the aforesaid two curves which, on a weight/time diagram preferably enclose an ideal curve of the variation in weight with the time of haemodialysis This curve is calculated prior to the haemodialysis and it may be modified during the haemodialysis in accordance with the progress of haemodialysis. The calculation is made with the aid of general data and data specific to the patient.

The apparatus of the invention may additionally provide supplementary data, corresponding for example, to the identification of the initial characteristics of the patient, or the values at any time of at least one parameter.

For a better understanding of the invention, and to show how the same can be carried into effect, reference will now be made, by way of example only, to the accompanying drawings, wherein:

FIG. 3 is another weight-time diagram showing the variation in weight of a patient with time during haemodialysis and the curves which indicate the acceptable limits of weight variation at any particular time during haemodialysis;

FIG. 4 is a schematic representation of a haemodialysis apparatus according to the invention;

Figure 1:
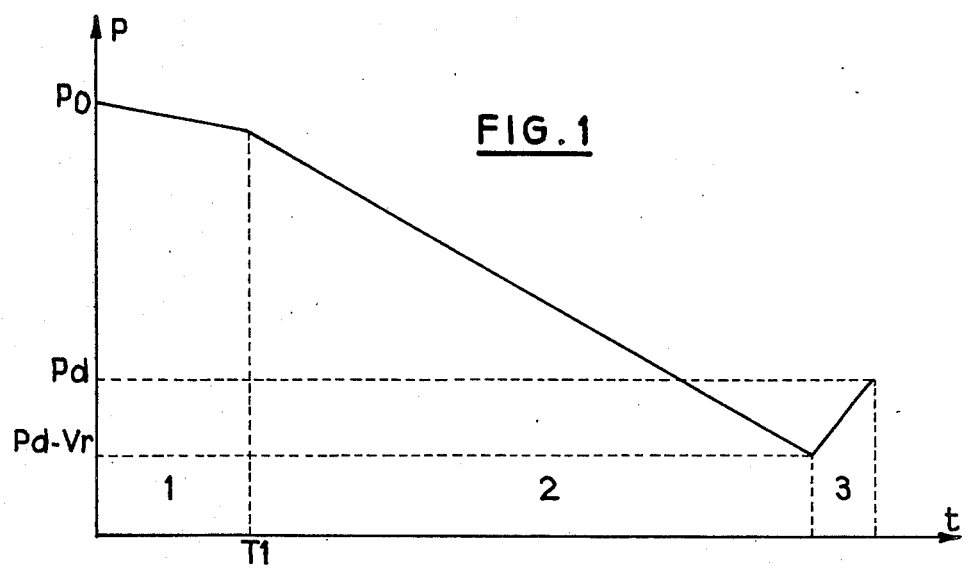
FIGS. 1 and 2 are weight-time diagrams showing examples of ideal weight variation curves during haemodialysis.

The adjustment of the haemodialysis conditions in the practice of this invention requires, firstly, the calculation of an ideal weight curve from the initial values of the dialysis parameters and the desired final weight and, secondly, the determination of the best manner of achieving the desired final values with the assistance of the dialysis parameter values determined at any instant.

The determination of the ideal weight curve will be dependent upon the nature of the contents of the haemodialyser which is used. For example, the curve may comprise three parts corresponding to a first dialysis period, a second dialysis period and a restoration period indicated in FIGS. 1 and 2 by the reference numerals 1, 2 and 3 respectively. During the first dialysis period, the rate of loss of weight is low when the artificial kidney contains an isotonic saline solution. The ideal ultrafiltration gradient is, in this case, low in relation to the mean gradient during the remainder of the dialysis. When the dialyser contains a macromolecular solution and not an isotonic saline solution, the rate of loss in weight may be constant during the two dialysis periods.

In this first dialysis period, five to ten minutes are devoted to checking the properties of the membrane of the dialyser before haemodialysis is commenced. Moreover, the rate of flow of blood on the counter pressure (outlet pressure of the blood) are set at low values so as to avoid the risk of rupture of blood vessels with the commencement of dialysis. This testing time is too short for it to have an appreciable influence on the theoretical curve and it may be disregarded.

During the second dialysis period, the loss in weight varies linearly with time.

The restoration period which commences when the dialysis proper is terminated, lasts for five minutes, during which the blood content of the haemodialyser and a connection tube between patient and haemodialyser is restored to the patient, possibly with addition of a volume of liquid (isotonic saline solution or macromolecular solution). The desired weight is determined after this restoration.

The calculation of the ideal curve before commencing a haemodialysis requires knowledge of a certain number of parameters. Certain of these parameters may undergo modification during the dialysis, for example, the desired final weight, the duration of the haemodialysis, the total weight of the perfusions and the provided perfusion time, this time being less than or equal to the dialysis time.

Fixed parameters to consider are the initial weight, the initial contents of the haemodialyser and the restoration volume on completion of dialysis. The restoration volume is equal to the sum of the volume of the dialyser which is constant and the volume of fluid used for emptying it when this fluid is a solution.

Figure 2:
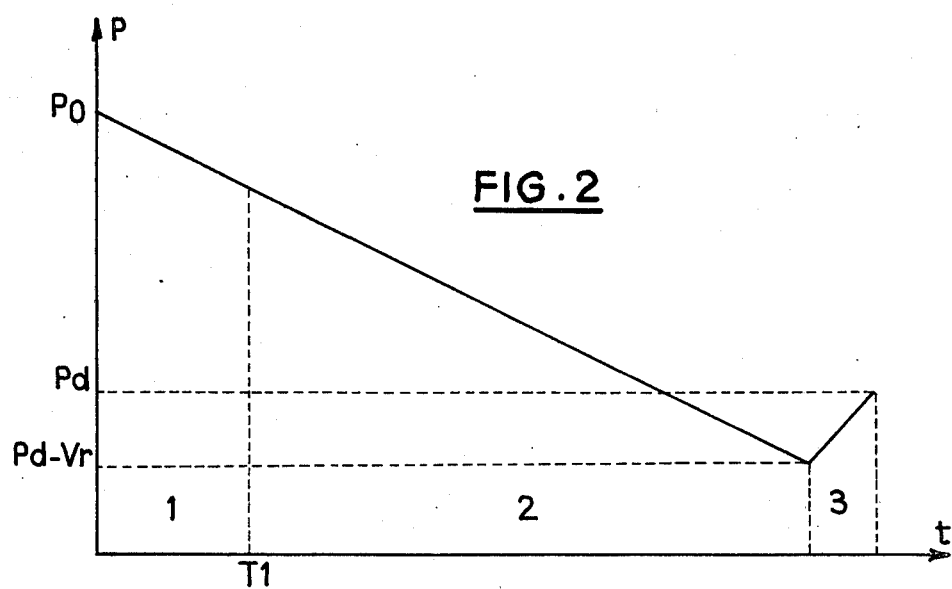

Referring next to FIGS. 1 to 3, these are curves in which body weight, P, is plotted to the ordinate axis against time t. In FIGS. 1 and 2, typical curves calculated in the manner set out hereinafter are shown, whereas in FIG. 3, two calculated and acceptable curves of the type shown in FIG. 2 are indicated by broken lines and between them lies a solid curve showing the actual change in body weight encountered during a haemodialysis during which tendency for body weight to increase has to be compensated for.

When the dialyser is initially filled with an isotonic saline solution, the ideal curve may have the form shown in FIG. 1, that is to say, it comprises three straight segments, namely a segment of negative slope a/n during the first dialysis period 1, a segment of negative slope a during a second dialysis period 2 and a segment of positive slope during the third period of restoration period 3.

FIG. 2 shows an ideal curve for a haemodialysis carried out when the apparatus is filled with a macromolecular solution. It is noted that in this case, the curve comprises a single straight segment of negative slope a during the two dialysis periods. The curves of FIGS. 1 and 2, given by way of example, correspond to the equations:

$$a = \frac{Pd - Vr - Pt}{Td - T1(1 - b) - bt}$$

$$u = -ab + \frac{Vp - Vt}{Tp - t}$$

in which
  Vp is the total weight of perfusion light provided,
  Vt is the weight of liquid perfused at any time,
  Vr is the weight of the restoration liquid,
  Pt is the initial weight of the patient,
  Pd is the desired weight,
  Td is the duration of the haemodialysis,
  T1 is the duration of the first haemodialysis period,
  Tp is the time during which perfusion is effected,
  t represents the time calculated from the commencement of dialysis,
  u represents the desired ultrafiltration rate,
  a is the rate of loss of weight during the second dialysis period, and
  b is a calculation parameter.

The total volume of the perfusion liquid provided is equal to the volume already perfused when Vp is greater than Vt or when t is greater than Tp. b represents the coefficient of slope of gradient reduction when t is smaller than T1 and when the dialyser is filled with saline solution. In other cases, b is equal to 1. Moreover, it should be noted that the fraction in the expression giving u has a zero value when t is greater than or equal to Tp.

In fact, during haemodialysis, it is not the rate of ultrafiltration which is followed, but the mean difference in pressures in the dialyser, that is to say, the difference between the means of the inlet and outlet pressures of dialysate. The relationship between this difference, P, in pressures and the rate of ultrafiltration u is given by the equation:

$$P = \alpha U + \beta$$

$\alpha$ and $\beta$ being constants determined by the construction of the haemodialysis apparatus.

The curves thus calculated permit the haemodialysis conditions to be regulated.

The general organisation of preferred apparatus according to this invention will now be described with reference to FIG. 4. A patient 10 is placed on a bed 12. He is connected to a blood compartment 16 of a haemodialyser 14 which comprises the blood compartment and a dialysate compartment 18 through a blood circuit which comprises a pump 20 which is optional and may be dispensed with, pressure sensors 20 and 24 positioned at the inlet and outlet respectively of the dialyser and a flow rate sensor 26. For dialysate there is a circuit which comprises an inlet pressure sensor 28 and an outlet pressure sensor 30, or an ultrafiltration sensor 32 which is also shown. When the return of the dialysate circuit is at atmospheric pressure, the sensor 30 may obviously be omitted. A control unit 34 is provided for regulation of the rate of perfusion of the patient.

The bed 12 of the patient is mounted on an electronic balance 36 of the analog type, which is connected to an analog-digital converter 38. In addition, the patient carries on his arm an arterial pressure sensor 40 which will be hereinafter described in greater detail by reference to FIG. 6.

The sensors 22, 24, 26, 28, 30 and 40, the control unit 34 and the converter 38 all transmit signals to a data processing unit or to a cabled or microprogrammed logic unit 42 which exchanges data with a display console 44, which may comprise a data input keyboard.

The various elements of the apparatus shown in FIG. 4 will now be described in greater detail. The sensors 22, 24, 28 and 30 may be of the type No. 8 805 marketed in France by Endevco, having an area of use of ±500 mmHg. These sensors comprise a part which is to be sterilised or discarded after use and a fixed part.

The blood flow sensor 26 may be a Doppler effect flow meter designed to measure the flow rate in the blood circulation tube. It will generally have a range of measurements from 30 to 500 cc/min, supplying a continuous analog voltage which can be transformed into numerical form for direct treatment by the data processing unit 42.

The ultrafiltration sensor 32 may take the form of an overflow dripping into a test tube positioned on a balance transmitting an analog signal in the case of certain haemodialysers, such as model "RP6" of Rhone- Poulenc. The sensitivity of this signal is preferably at least 50 g, the maximum weight to be measured being of the order of 8 kg.

The control unit 34 for regulating the perfusion may comprise an automatic perfuser or drip known as the Braun "Infusomat". This apparatus comprises a peristaltic pump driven by a stepping motor, which is itself piloted by a pulse generator. The rate of perfusion is for example adjustable continuously between 5 and 1000 cc/hour.

The balance 36 may be of the "Fresenius" electronic type, comprising a movable platform connected by a cable to a monitor. Its sensitivity will need to be 50 g up to a total load of 200 kg. It enables variations of ±10 kg relative to the initial weight to be followed and it transmits an analog signal to the converter 38.

Figure 6:
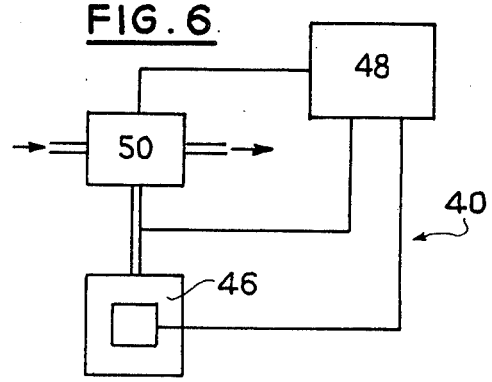
FIG. 6 is a schematic diagram of an arterial pressure sensor operating by a bloodless procedure as required by the process according to the invention.

As can be seen from FIG. 6, the sensor 40 for determining arterial pressure comprises a sphygmanometer 46, for example of the Siemens "Diasyst" type, a control unit 48 and an inflation valve 50. The control unit 48 regulates the inflation and the deflation of the arm of the sphygmanometer in response to signals from the data processing unit 42 and is unable to permit the measurement of the pulse, the systolic pressure and the diastolic pressure to be effected in the manner of a conventional sphygmanometer. This apparatus is preferably of a completely automatic type.

Figure 5:
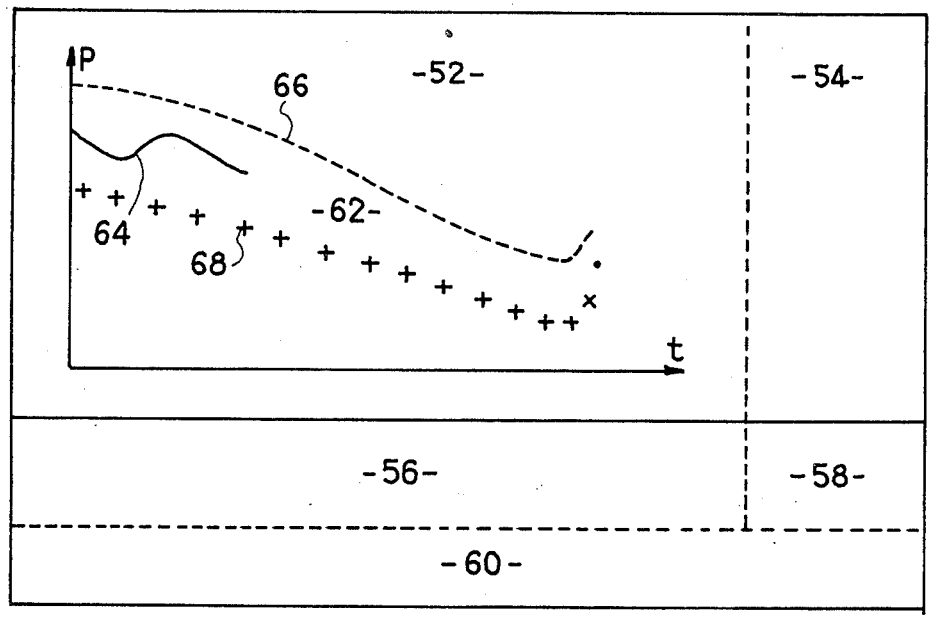
FIG. 5 represents the screen of the display console of the apparatus of FIG. 4, during a haemodialysis.

The data processing unit 42 receives all the signals from the sensors and exchanges the data with the display console 44 to be hereinafter described. In addition, it transmits the orders indicated by the arrows provided with a small circle on FIG. 4. The console 44 has, for example, a screen whose appearance is indicated in FIG. 5. The screen comprises a first zone 52, designed to indicate the name of the patient, the number of the session, the number of the bed, the hour and other such administrative particulars. Zone 54 indicates the initial data in relation to the haemodialyser, the provided time for the session in relation to the haemodialyser, the provided time for the session, the initial weight of the patient, the desired weight of the patient and various risk factors. Zone 56 indicates data pertained to the haemodialysis such as difference in weight, blood pressure, pulse, rate of flow of blood and ultrafiltration rate. Zone 58 provides an area in which an alarm condition for the patient can be indicated or warning can be given of an alarm condition for another bed to which the apparatus is connected to allow a full display of information pertaining to that bed to be presented on the console. Zone 60 is a dialogue zone.

A major part of the screen is occupied by a screen 62 which shows the actual variation in weight of the patient as a function of time. This curve 64 lies between two curves 66 and 68 which define accessible maximum and minimum weight ranges and are calculated as previously described.

During a haemodialysis operation, an operator introduced through the keyboard associated with the console the file number of the patient, in the form of seven alphanumerical characters, his name or his shortened name, the date, etc. All these parameters may or may not be arranged on a sequential mass periphery for use during each operation to which a patient is subject.

Certain parameters, such as initial weight and arterial pressure are directly recorded by means of the sensors. Others are asked for by means of the console, then arranged in a memory for the duration of the supervision, these parameters being, for example, the desired weight, the type of haemodialyser being used and its contents, the restoration volume, the duration of the session, the frequency of supervision, the degree of supervision, that is to say the frequency of supervision, the degree of supervision, that is to say the spacing of the curves which define the ranges, and the provided volume and speed of the perfusions.

The apparatus indicates alarm conditions. It is possible initially to classify them as minor alarms and major alarms. The minor alarms do not necessitate any immediate action and, for example, do not modify the frequency of utilisation of the data. They are indicated by a visual signal, for example, a flashing arrow on the console.

The major alarms necessitate immediate action by the medical staff and they can cause a modification in the frequency of acceptance of the data. In addition, they cause the appearance of data in the alarm zone 58 of the console.

The different courses of alarm are concerned, for example, with the weight, the arterial blood pressure and the pulse, the rate of flow of the blood, the pressures in the different circuits of the haemodialyser and the ultrafiltration conditions. For example, the data processing unit may verify the fact that the weight at the time falls within the range as provided and possibly indicate an alarm condition. However, it is able to disregard a too large variation in weight between the two acceptances of data, for example subsequent to a book being placed on the bed of a patient.

Minimum and maximum values of the arterial pressure, depending on the arterial pressure at the commencement of the dialysis, are calculated at the commencement of the session, as a function of the degree of risk, and then with each change in the degree of risk.

Provision can also be made for an alarm range in respect of the pulse to be given when too greater a variation from the initial value of the pulse occurs.

The extreme values of the rate of flow of blood are constant parameters which can be stored in the memory and can also lead to the establishment of an alarm condition.

Four pressure readings of the haemodialyser can lead to establishment of an alarm condition. These four pressures are the inlet and outlet pressures of the blood and of the dialysate. In coil dialysers, the inlet and outlet pressures of the dialysate are both practically zero. The ranges of these values for actuating the alarm are stored in a memory so that each time the difference in pressures inside the dialyser is spaced from a calculated value, an alarm condition is indicated, this difference in internal pressures in the dialyser is equal to the difference between the mean of the inlet and outlet pressures of the blood circuit and that of the inlet and outlet pressures of the dialysate circuit. The doctor is able to increase the difference in pressures by increasing the counter pressure, that is to say, the pressure of the blood, or by increasing the rate of flow of blood.

In the case of the artifical kidney "RP6", this difference in pressures does not apply and the control parameter is the rate of variation of the ultrafiltration rate, measured with respect to the recommended values.

The acceptance of the data can be effected at difference frequencies. For example, the weight can be measured every minute, whatever may be the conditions. On the other hand, the arterial pressure and the pulse which are measured every fifteen minutes under normal conditions, can be measured every five minutes or even every minute. The parameters relating to blood flow, the perfusion flow, pressures and the ultrafiltration flow rate are normally measured every five or ten minutes, but can be measured every minute under alarm conditions.

Although the heaemodialyser apparatus of the invention has been described hereinabove primarily with respect to its use as an artificial kidney, it is pointed out that the method and apparatus of the invention are not limited in their application to the treatment of chronic renal deficiency. Haemodialysers are also utilised as "artificial pancreases". What is then involved is a treatment wherein a dosage of insulin is supplied to the blood of a diabetic and the amount of insulin present is compared, preferably automatically, with a reference value and further insulin is supplied to the blood of the diabetic if necessary. The apparatus according to the invention permits the automatic correction of the insulin supply as a function of the operation of the artificial pancreas. Consequently, data can be made available for calculating a haemodialysis curve, because these data are correlated to the variations in weight.

Although an apparatus has been described herein which ensures the control of a large number of parameters, it must be noted that variations in weight constitute the fundamental parameter on which is based the control of haemodialysis. These variations in weight are preferably determined accurately, measurements being to within 50 g.

What is claimed is:
1. A method of regulating haemodialysis conditions while simultaneously subjecting a patient to ultrafiltration of the blood, which method comprises:
   circulating the blood of the patient to and from one side of a membrane of a haemodialyser,
   circulating a haemodialysis solution to and from the other side of the said membrane of the haemodialyser,
   supplying physiologically acceptable fluid to the patient by perfusion,
   monitoring variations in the weight of the patient during the haemodialysis,
   determining a validity zone defined by two weight-/time curves defining at any given moment an area of weight values,
   comparing variations in weight with said area at any one moment, for generating a control signal, and
   controlling at least a parameter determining the course of ultrafiltration according to said control signal.
2. A method as claimed in claim 1, wherein said control signal is generated according the difference between the current weight value and the weight value corresponding to an ideal curve calculated to lie within said validity zone.
3. A method as claimed in claim 2, wherein said calculated ideal curve is plotted in accordance with the formula:

$$a = \frac{Pd - Vr - Pt}{Td - T1(1b) - bt}$$

$$u = -ab + \frac{Vp - Vt}{Tp - t}$$

in which
Vp is the total weight of perfusion liquid provided,
Vt is the weight of liquid perfused at any time,
Vr is the weight of the restoration liquid,
Pt is the initial weight of the patient,
Pd is the desired weight,
Td is the duration of the haemodialysis,
T1 is the duration of the first haemodialysis period,
Tp is the time during which perfusion is effected,
t represents the time calculated from the commencement of dialysis,
u represents the desired ultrafiltration rate,
a is the rate of loss of weight during the second dialysis period, and
b is a calculation parameter.
4. Method as claimed in claim 1, further including monitoring the arterial pressure of the patient
   comparing the monitored arterial pressure with a set pressure, and
   controlling an alarm means when a difference between the monitored arterial pressure and the set pressure is above a threshold.
5. A process as claimed in claim 4, wherein said arterial pressure is determined by a bloodless procedure.
6. A haemodialysis apparatus for effecting dialysis of the blood by ultrafiltration, comprising:
   a haemodialyser having membrane means separating a blood compartment for a dialysis solution compartment,
   means for causing the circulation of the blood of a patient and a haemodialysis solution on either side of said membrane,
   a perfusion arrangement for a patient whose blood is to undergo haemodialysis,
   at least one sensor of a parameter related to the weight of a patient for providing a signal representing variations in the weight of the patient,
   means for comparing the signal of variations in weight with an area of weight values defined by plotting maximum and minimum acceptable weights of the patient at each time within a haemodialysis period during which the haemodialyser is to be employed, to give a control signal when the signal of weight variation is not within said area, and
   means for controlling at least a parameter determining the course of ultrafiltration according to said control signal.
7. Apparatus as claimed in claim 6, further including means for monitoring the arterial pressure of the patient,
   means for comparing the monitored arterial pressure with a set pressure, and
   means for controlling an alarm means when a difference between the monitored arterial pressure and the set pressure is above a threshold.
8. Apparatus as claimed in claim 7, wherein means for monitoring the arterial pressure detects arterial pressure by a bloodless procedure.
9. Apparatus as claimed in claim 8, wherein said sensor is adapted to detect Korotkoff sounds.
10. Apparatus as claimed in claim 8, wherein said sensor is adapted to measure Doppler effect as a means of indicating arterial pressure.
11. Apparatus as claimed in claim 6, which additionally comprises an alarm indicator controlled by the control signal and adapted to indicate an alarm condition.
12. Apparatus as claimed in claim 6, wherein means for controlling at least a parameter determining the course of ultrafiltration controls at least a parameter selected in the group comprising the weight of liquid withdrawn by ultrafiltration, the pressures of the blood at the inlet and the outlet of the haemodialyser, the pressures of the dialysis solution at the inlet and the outlet of the haemodialyser, the flow rate of the blood in the haemodialyser, and the rate of perfusion.

* * * * *